United States Patent
Nakagawa et al.

(10) Patent No.: US 12,134,316 B2
(45) Date of Patent: Nov. 5, 2024

(54) STATE DETECTION DEVICE, STATE DETECTION SYSTEM, AND STATE DETECTION METHOD

(71) Applicant: SONY GROUP CORPORATION, Tokyo (JP)

(72) Inventors: Kei Nakagawa, Tokyo (JP); Shin Kitano, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 397 days.

(21) Appl. No.: 17/593,376

(22) PCT Filed: Mar. 10, 2020

(86) PCT No.: PCT/JP2020/010190
§ 371 (c)(1),
(2) Date: Sep. 16, 2021

(87) PCT Pub. No.: WO2020/195770
PCT Pub. Date: Oct. 1, 2020

(65) Prior Publication Data
US 2022/0161654 A1    May 26, 2022

(30) Foreign Application Priority Data
Mar. 27, 2019    (JP) ................. 2019-060217

(51) Int. Cl.
*B60K 28/06* (2006.01)
*B60K 35/00* (2024.01)
(Continued)

(52) U.S. Cl.
CPC ............ *B60K 28/066* (2013.01); *B60K 35/00* (2013.01); *G06T 7/73* (2017.01); *B60K 35/10* (2024.01);
(Continued)

(58) Field of Classification Search
CPC ............ B60K 28/066; B60K 35/00; B60K 2370/149; B60K 2370/176; G06T 7/73;
(Continued)

(56) References Cited

U.S. PATENT DOCUMENTS 6,575,902 B1 * 6/2003 Burton ............... B60W 40/08
                                                           600/595
6,624,849 B1    9/2003 Nomura
(Continued)

FOREIGN PATENT DOCUMENTS

CN    105654753 A    6/2016
CN    105894733 A    8/2016
(Continued)

OTHER PUBLICATIONS

International Search Report and Written Opinion of PCT Application No. PCT/JP2020/010190, issued on Jun. 9, 2020, 09 pages of ISRWO.

*Primary Examiner* — Omeed Alizada
(74) *Attorney, Agent, or Firm* — CHIP LAW GROUP

(57) ABSTRACT

A state of a driver is detected more quickly. A state detection device according to an embodiment is provided with a first solid-state imaging device provided with a plurality of pixels arranged in a matrix, the first solid-state imaging device that detects, according to a light amount incident on each of the pixels, occurrence of an event in the pixel, and a state detection unit that detects a state of a driver on the basis of the occurrence of the event detected by the first solid-state imaging device.

11 Claims, 13 Drawing Sheets

(51) Int. Cl.
*B60K 35/10* (2024.01)
*B60K 35/28* (2024.01)
*G06T 7/73* (2017.01)

(52) U.S. Cl.
CPC ........ *B60K 35/28* (2024.01); *B60K 2360/149* (2024.01); *B60K 2360/176* (2024.01); *B60Y 2200/11* (2013.01); *G06T 2207/30041* (2013.01); *G06T 2207/30201* (2013.01); *G06T 2207/30268* (2013.01)

(58) Field of Classification Search
CPC . G06T 2207/30041; G06T 2207/30201; G06T 2207/30268; G06T 2207/10021; G06T 2207/10048; G06T 2207/30196; G06T 2207/30248; G06T 7/20; G06T 7/593; B60Y 2200/11; H04N 23/00; H04N 25/50; H04N 7/18; H04N 23/60; A61B 3/113; A61B 5/1128; A61B 5/18; G06V 40/193; G06V 20/597
See application file for complete search history.

(56) References Cited

U.S. PATENT DOCUMENTS

| | | | | |
|---|---|---|---|---|
| 9,557,856 | B2* | 1/2017 | Send | G01S 11/12 |
| 2010/0077421 | A1* | 3/2010 | Cohen | G07C 9/37 |
| | | | | 348/370 |
| 2018/0167575 | A1 | 6/2018 | Watanabe | |
| 2019/0056498 | A1* | 2/2019 | Sonn | G01S 17/931 |
| 2019/0188827 | A1* | 6/2019 | Mitani | H04N 23/80 |

FOREIGN PATENT DOCUMENTS

| | | |
|---|---|---|
| CN | 107077601 A | 8/2017 |
| CN | 108860153 A | 11/2018 |
| CN | 109155829 A | 1/2019 |
| CN | 110546945 A | 12/2019 |
| JP | 10-86696 A | 4/1998 |
| JP | 2011-159214 A | 8/2011 |
| JP | 2018-501531 A | 1/2018 |
| JP | 2018-186478 A | 11/2018 |
| JP | 2019-103744 A | 6/2019 |
| KR | 10-2017-0063643 A | 6/2017 |
| WO | 2016/053886 A1 | 4/2016 |
| WO | 2018/198691 A1 | 11/2018 |
| WO | 2019/117247 A1 | 6/2019 |

* cited by examiner

STATE DETECTION DEVICE, STATE DETECTION SYSTEM, AND STATE DETECTION METHOD

CROSS REFERENCE TO RELATED APPLICATIONS

This application is a U.S. National Phase of International Patent Application No. PCT/JP2020/010190 filed on Mar. 10, 2020, which claims priority benefit of Japanese Patent Application No. JP 2019-060217 filed in the Japan Patent Office on Mar. 27, 2019. Each of the above-referenced applications is hereby incorporated herein by reference in its entirety.

TECHNICAL FIELD

The present disclosure relates to a state detection device, a state detection system, and a state detection method.

BACKGROUND ART

Conventionally, there has been developed a drowsy driving prevention device that determines whether or not a driver is dozing from an image obtained by imaging the driver and, in a case where the driver is dozing, issues an alarm to the driver to prevent drowsy driving.

CITATION LIST

Patent Document

Patent Document 1: Japanese Patent Application Laid-Open No. 10-86696

SUMMARY OF THE INVENTION

Problems to be Solved by the Invention

In a general drowsy driving prevention device, it is determined whether or not a driver is dozing by analyzing image data read from a camera at a predetermined frame rate. Therefore, a data processing amount required for detecting a state of the driver is large, and it is difficult to quickly determine whether or not the driver is dozing.

Therefore, the present disclosure proposes a state detection device, a state detection system, and a state detection method capable of detecting a state of a driver more quickly.

Solutions to Problems

In order to solve the above-described problem, a state detection device according to an embodiment according to the present disclosure is provided with a first solid-state imaging device provided with a plurality of pixels arranged in a matrix, the first solid-state imaging device that detects, according to a light amount incident on each of the pixels, occurrence of an event in the pixel, and a state detection unit that detects a state of a driver on the basis of the occurrence of the event detected by the first solid-state imaging device.

MODE FOR CARRYING OUT THE INVENTION

Figure 1:
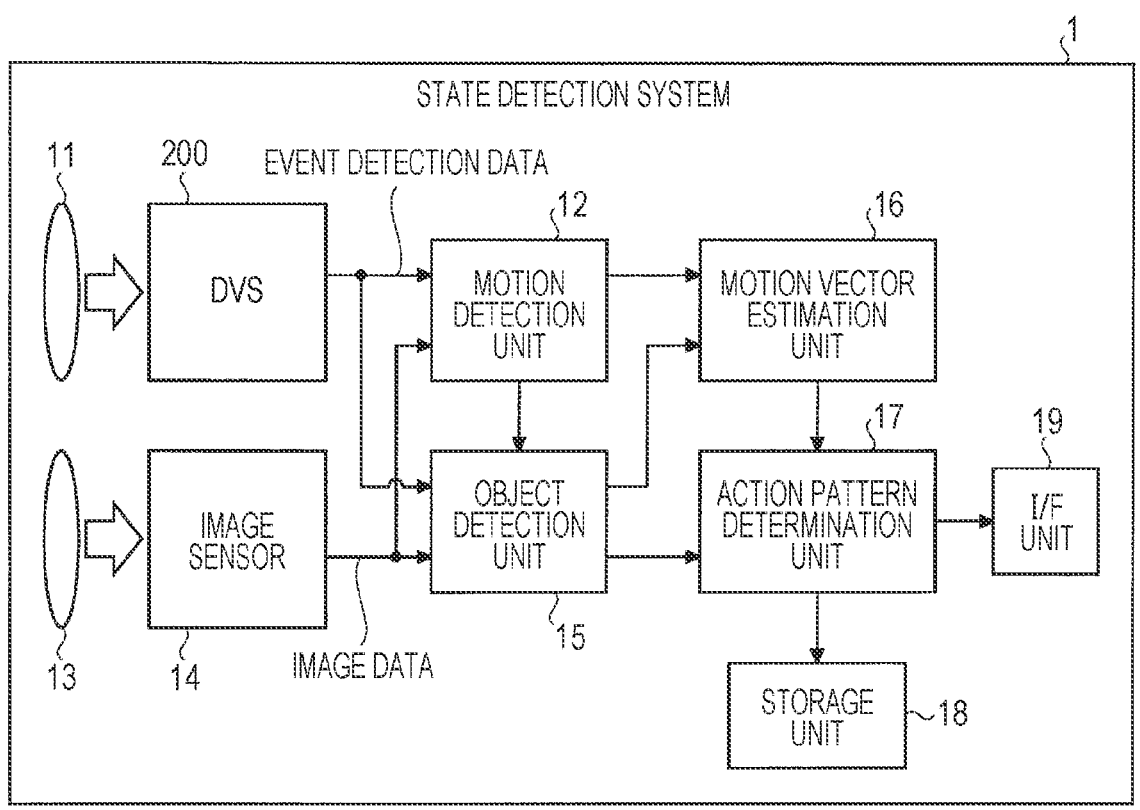
FIG. 1 is a block diagram illustrating a schematic configuration example of a state detection device (system) according to a first embodiment.

Hereinafter, an embodiment of the present disclosure is described in detail with reference to the drawings. Note that, in the following embodiments, the same parts are denoted by the same reference numerals, and the description thereof is not repeated.

Furthermore, the present disclosure is described according to the following item order.

1. First Embodiment
1.1 Configuration Example of State Detection Device (or System)
1.2 Configuration Example of DVS
1.3 Configuration Example of Unit Pixel
1.4 Configuration Example of Address Event Detection Unit
1.4.1 Configuration Example of Current-voltage Conversion Unit 1.4.2 Configuration Example of Subtractor and Quantizer
1.5 Application Example to Mobile Body
1.6 Arrangement Example of Imaging Unit
1.7 Arrangement Example of Driver's State Detection Unit (DVS)
1.8 State Detection Operation Example
1.9 Action and Effect
2. Second Embodiment
2.1 State Detection Operation Example
2.2 Action and Effect
2.3 Variation 1. First Embodiment First, a first embodiment is described in detail with reference to the drawings.
1.1 Configuration Example of State Detection Device (or System)

FIG. 1 is a block diagram illustrating a schematic configuration example of a state detection device (or a state detection system, hereinafter, referred to as the state detection device) according to the first embodiment. As illustrated in FIG. 1, a state detection device 1 is provided with, for example, an imaging lens 11, a dynamic vision sensor (DVS) (first solid-state imaging device) 200, a motion detection unit 12, an imaging lens 13, an image sensor (second solid-state imaging device) 14, an object detection unit 15, a motion vector estimation unit 16, an action pattern determination unit 17, a storage unit 18, and an interface (I/F) unit 19.

The DVS 200 is a sensor for detecting a state of a driver, and is an asynchronous image sensor in which a detection circuit that detects that a light reception amount exceeds a threshold in real time as an address event is provided for each pixel.

In a general DVS, a so-called event-driven drive system is adopted in which it is detected whether or not the address event occurs for each unit pixel, and in a case where the occurrence of the address event is detected, a pixel signal is read from the unit pixel in which the address event occurs. Furthermore, since a read operation is executed on the unit pixel in which the occurrence of the address event is detected in the general DVS, this has a characteristic that reading at a very high speed may be performed as compared with a synchronous image sensor in which the read operation is executed on all the unit pixels, and a data amount read as that of one frame is small.

Therefore, by using the DVS 200 as the sensor for detecting the state of the driver, the state of the driver may be detected more quickly. It is also possible to reduce power consumption by reducing the data amount when detecting the state.

Note that the unit pixel in this description is a minimum unit of a pixel including one photoelectric conversion element (also referred to as a light receiving element), and corresponds to each dot in the image data read from the image sensor, for example. Furthermore, the address event is an event that occurs in each address assigned to each of a plurality of unit pixels arranged in a two-dimensional lattice pattern such as, for example, an event that a current value of a current (hereinafter, referred to as a photocurrent) based on a charge generated in the photoelectric conversion element or a change amount thereof exceeds a certain threshold.

In this embodiment, the DVS 200 detects the occurrence of the address event on the basis of an amount of incident light, and generates address information for specifying the unit pixel in which the occurrence of the address event is detected as event detection data. The event detection data may include time information such as a time stamp indicating a timing at which the occurrence of the address event is detected. Furthermore, the generated event detection data is input to the motion detection unit 12 and the object detection unit 15.

In contrast, the image sensor 14 may be various image sensors capable of obtaining the image data such as a charge coupled device (CCD) image sensor and a complementary metal-oxide-semiconductor (CMOS) image sensor, for example. The image data obtained by the image sensor 14 is input to the motion detection unit 12 and the object detection unit 15.

Note that the DVS 200 and the image sensor 14 may be arranged in proximity to each other in the same direction so as to image substantially the same angle of view, for example.

The imaging lens 11 is an example of an optical system that condenses incident light and forms an image thereof on a light receiving surface of the DVS 200. The light receiving surface may be a surface on which photoelectric conversion elements are arranged in the DVS 200.

As is the case with the imaging lens 11, the imaging lens 13 is an example of an optical system that condenses incident light and forms an image thereof on a light receiving surface of the image sensor 14. The light receiving surface may be a surface on which photoelectric conversion elements are arranged in the image sensor 14.

The motion detection unit 12 detects motion of an object present in the angle of view of the DVS 200 on the basis of the event detection data input from the DVS 200, for example. For example, the motion detection unit 12 creates one frame data on the basis of the event detection data input within a predetermined period, and detects motion of a region in a frame from the created frame data. At that time, the motion detection unit 12 may check whether the detected motion is the motion of the object or erroneous detection and the like using the image data input from the image sensor 14. A result of the motion detection is input to, for example, the object detection unit 15 and the motion vector estimation unit 16. Note that a cycle at which the motion detection unit 12 generates the frame data from the event detection data may be the same as or shorter than a cycle (frame rate) at which the image sensor 14 obtains the image data.

The object detection unit 15 detects the object the motion of which is detected by the motion detection unit 12 on the basis of the event detection data input from the DVS 200, for example. For example, the object detection unit 15 creates one frame data on the basis of the event detection data input within a predetermined period, and detects the object in a frame from the created frame data. At that time, the object detection unit 15 may detect the object by combining the event detection data input from the DVS 200 and the image data input from the image sensor 14. A result of the object detection is input to, for example, the motion vector estimation unit 16 and the action pattern determination unit 17. Note that a cycle at which the object detection unit 15 generates the frame data from the event detection data may be, for example, the same as or different from the cycle at which the motion detection unit 12 generates the frame data from the event detection data. For example, the object detection unit 15 may generate the frame data at the same cycle as the frame rate at which the image sensor 14 obtains the image data.

The motion vector estimation unit 16 estimates, for example, on the basis of the motion detected by the motion detection unit 12 of the object detected by the object detection unit 15, a motion vector of the object. When estimating the motion vector of the object, a general method of estimating the motion vector from a motion amount of the region between the frames may be used. Hereinafter, in order to simplify the description, "estimating the motion vector of the object" is referred to as "detecting the motion of the object". The estimated motion vector is input to the action pattern determination unit 17, for example.

The action pattern determination unit 17 determines an action pattern of a device such as a vehicle on which the state detection system 1 is mounted on the basis of the motion of the object estimated by the motion vector estimation unit 16, for example.

The storage unit 18 stores various programs and data necessary for the action pattern determination unit 17 to determine the action pattern.

The I/F unit 19 is, for example, an interface for transmitting and receiving data to and from the outside via a bus and the like.

In the above-described configuration, the motion detection unit 12, the object detection unit 15, and the motion vector estimation unit 16 serve as a state detection unit that detects a state of a person or an object such as a driver.

Machine learning using a learned model stored in advance in a memory and the like may be used for the motion detection by the motion detection unit 12, the object detection by the object detection unit 15, the estimation of the motion vector by the motion vector estimation unit 16, and the determination of the action pattern by the action pattern determination unit 17. However, there is no limitation; for example, in the object detection by the object detection unit 15, a technology such as pattern matching for specifying the object from matching between a feature point extracted from the event detection data or the image data and a feature point stored in advance in the memory and the like may be used.

1.2 Configuration Example of DVS

Figure 2:
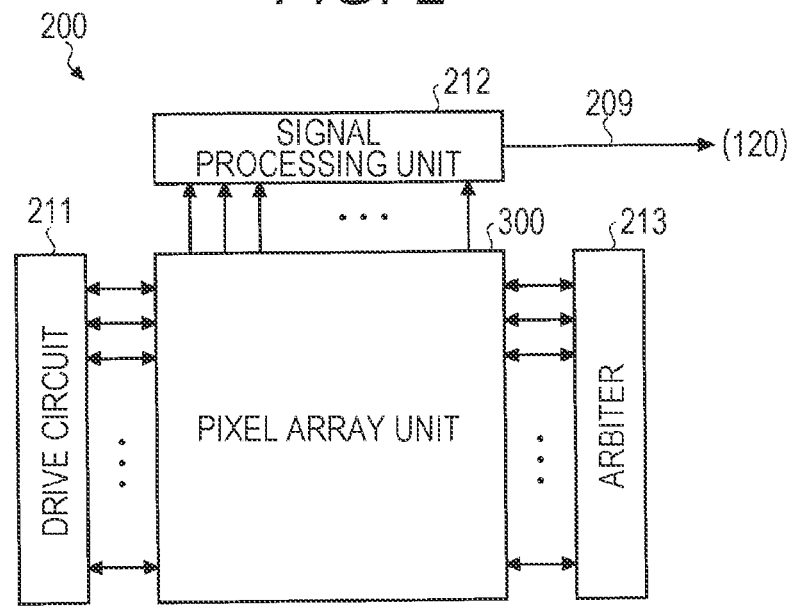
FIG. 2 is a block diagram illustrating a functional configuration example of a DVS according to the first embodiment.

Subsequently, a configuration example of the DVS 200 is described in detail with reference to the drawings. FIG. 2 is a block diagram illustrating a functional configuration example of the DVS according to the first embodiment. As illustrated in FIG. 2, the DVS 200 is provided with a drive circuit 211, a signal processing unit 212, an arbiter 213, and a pixel array unit 300.

In the pixel array unit 300, a plurality of unit pixels is arranged in a two-dimensional lattice pattern. As is described later in detail, the unit pixel includes, for example, a photoelectric conversion element such as a photodiode, and a pixel circuit (in this embodiment, corresponding to an address event detection unit 400 described later) that detects whether or not the address event occurs on the basis of whether or not a current value of a photocurrent by a charge generated in the photoelectric conversion element or a change amount thereof exceeds a predetermined threshold. Here, the pixel circuit may be shared by a plurality of photoelectric conversion elements. In this case, each unit pixel includes one photoelectric conversion element and a shared pixel circuit.

A plurality of unit pixels of the pixel array unit 300 may be grouped into a plurality of pixel blocks each including a predetermined number of unit pixels. Hereinafter, a set of unit pixels or pixel blocks arranged in a horizontal direction is referred to as a "row", and a set of unit pixels or pixel blocks arranged in a direction perpendicular to the row is referred to as a "column".

When the occurrence of the address event is detected in the pixel circuit, each unit pixel outputs a request for reading a signal from the unit pixel to the arbiter 213.

The arbiter 213 arbitrates the request from one or more unit pixels, and transmits a predetermined response to the unit pixel that issues the request on the basis of a result of the arbitration. The unit pixel that receives this response outputs a detection signal indicating the occurrence of the address event to the drive circuit 211 and the signal processing unit 212.

The drive circuit 211 sequentially drives the unit pixel that outputs the detection signal, thereby allowing the unit pixel in which the occurrence of the address event is detected to output a signal according to the light reception amount, for example, to the signal processing unit 212. Note that the DVS 200 may be provided with an analog-digital converter for converting a signal read from a photoelectric conversion element 333 to be described later into a signal of a digital value according to a charge amount thereof, for example, for each unit pixel or a plurality of unit pixels, or for each column.

The signal processing unit 212 executes predetermined signal processing on the signal input from the unit pixel, and supplies a result of the signal processing as the event detection data to the data processing unit 120 via the signal line 209. Note that, as described above, the event detection data may include the address information of the unit pixel in which the occurrence of the address event is detected, and the time information such as the time stamp indicating the timing at which the address event occurs.

1.3 Configuration Example of Unit Pixel

Figure 3:
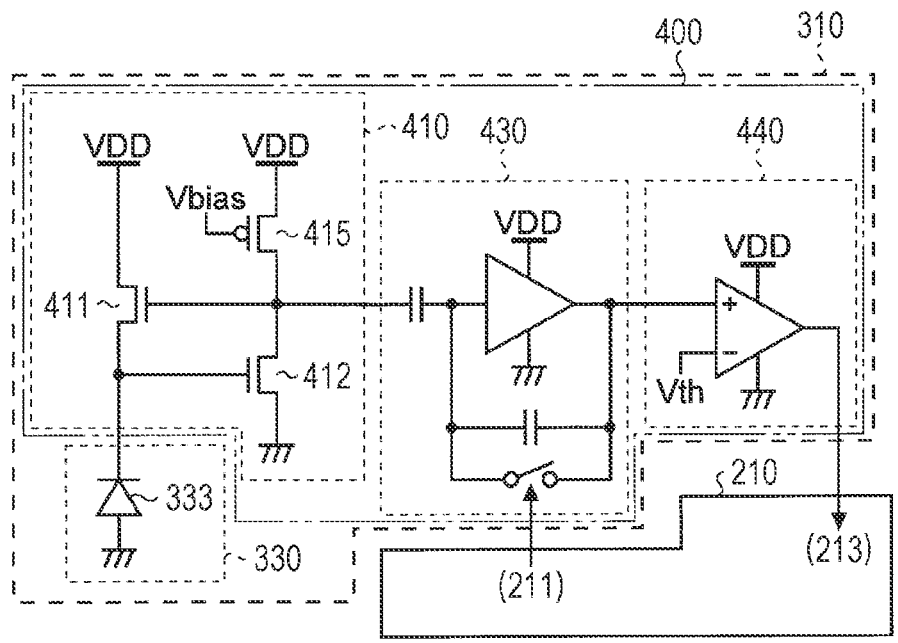
FIG. 3 is a circuit diagram illustrating a schematic configuration example of a unit pixel according to the first embodiment.

Subsequently, a configuration example of a unit pixel 310 is described. FIG. 3 is a circuit diagram illustrating a schematic configuration example of the unit pixel according to the first embodiment. As illustrated in FIG. 3, the unit pixel 310 is provided with, for example, a light reception unit 330 and the address event detection unit 400. Note that a logic circuit 210 in FIG. 3 may be, for example, a logic circuit including the drive circuit 211, the signal processing unit 212, and the arbiter 213 in FIG. 2.

The light reception unit 330 is provided with, for example, the photoelectric conversion element 333 such as a photodiode, and an output thereof is connected to the address event detection unit 400.

The address event detection unit 400 is provided with, for example, a current-voltage conversion unit 410 and a subtractor 430. However, the address event detection unit 400 is provided with a buffer, a quantizer, and a transfer unit in addition to them. The address event detection unit 400 is described later in detail with reference to FIG. 5 and the like.

In such a configuration, the photoelectric conversion element 333 of the light reception unit 330 photoelectrically converts the incident light to generate the charge. The charge generated in the photoelectric conversion element 333 is input to the address event detection unit 400 as the photocurrent of the current value according to the charge amount.

1.4 Configuration Example of Address Event Detection Unit

Figure 4:
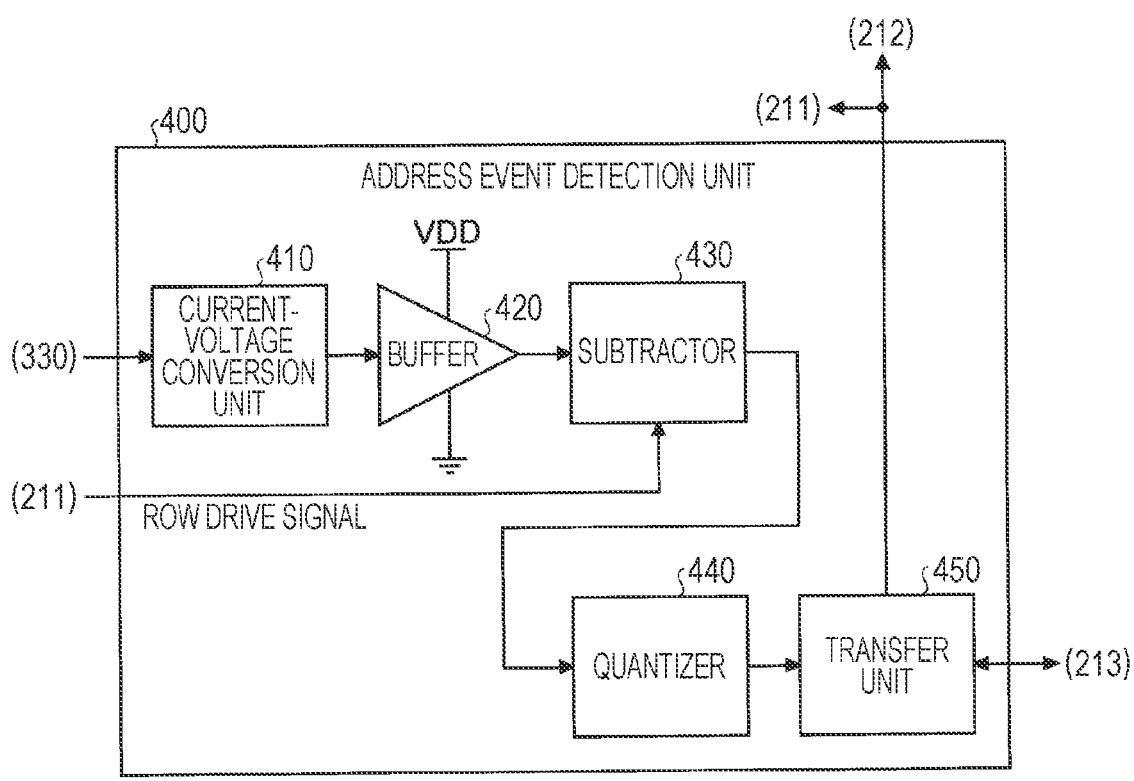
FIG. 4 is a block diagram illustrating a schematic configuration example of an address event detection unit in the first embodiment.

FIG. 4 is a block diagram illustrating a schematic configuration example of the address event detection unit in the first embodiment. As illustrated in FIG. 4, the address event detection unit 400 is provided with a buffer 420 and a transfer unit 450 in addition to the current-voltage conversion unit 410, the subtractor 430, and a quantizer 440 illustrated also in FIG. 3.

The current-voltage conversion unit 410 converts the photocurrent from the light reception unit 330 into a voltage signal of a logarithm thereof, and outputs the voltage signal generated by this to the buffer 420.

The buffer 420 corrects the voltage signal from the current-voltage conversion unit 410 and outputs the corrected voltage signal to the subtractor 430.

The subtractor 430 lowers a voltage level of the voltage signal from the buffer 420 according to a row drive signal from the drive circuit 211, and outputs the lowered voltage signal to the quantizer 440.

The quantizer 440 quantizes the voltage signal from the subtractor 430 into a digital signal, and outputs the digital signal generated by this to the transfer unit 450 as the detection signal.

The transfer unit 450 transfers the detection signal from the quantizer 440 to the signal processing unit 212 and the like. For example, when the occurrence of the address event is detected, the transfer unit 450 outputs to the arbiter 213 a request for requesting transmission of the detection signal of the address event from the transfer unit 450 to the drive circuit 211 and the signal processing unit 212. Then, upon receiving a response to the request from the arbiter 213, the transfer unit 450 outputs the detection signal to the drive circuit 211 and the signal processing unit 212.

1.4.1 Configuration Example of Current-voltage Conversion Unit

The current-voltage conversion unit 410 in the configuration illustrated in FIG. 4 may be, for example, a so-called source follower current-voltage conversion unit provided with an LG transistor 411, an amplification transistor 412, and a constant current circuit 415 as illustrated in FIG. 3. However, there is no limitation; this may also be a so-called gain boost current-voltage converter provided with two LG transistors 411 and 413, two amplification transistors 412 and 414, and the constant current circuit 415 as illustrated in FIG. 5, for example.

As illustrated in FIG. 3, a source of the LG transistor 411 and a gate of the amplification transistor 412 are connected to, for example, a cathode of the photoelectric conversion element 333 of the light reception unit 330. A drain of the LG transistor 411 is connected to a power supply terminal VDD, for example.

Furthermore, for example, a source of the amplification transistor 412 is grounded, and a drain thereof is connected to the power supply terminal VDD via the constant current circuit 415. The constant current circuit 415 may include, for example, a load MOS transistor such as a P-type metal-oxide-semiconductor (MOS) transistor.

Figure 5:
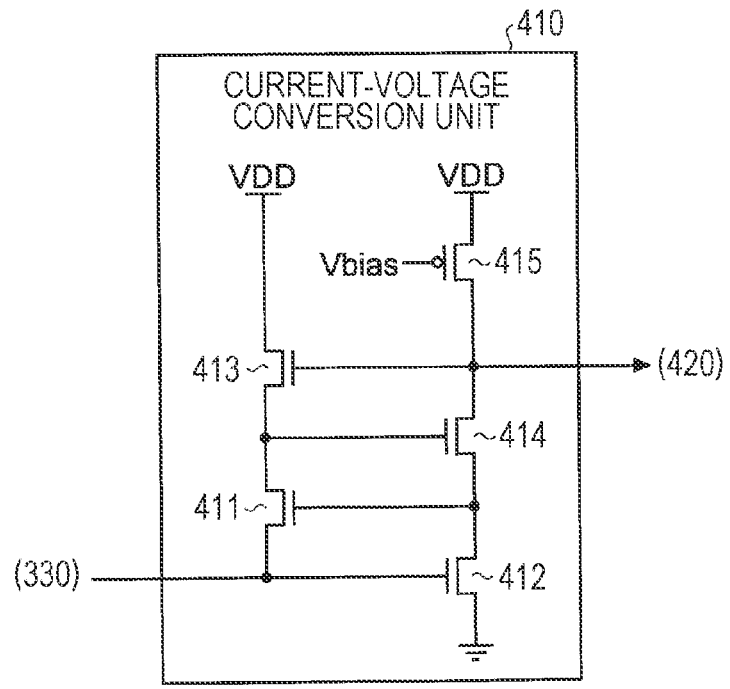
FIG. 5 is a circuit diagram illustrating another example of a current-voltage conversion unit according to the first embodiment.

In contrast, in a case of the gain boost type, as illustrated in FIG. 5, the source of the LG transistor 411 and the gate of the amplification transistor 412 are connected to, for example, the cathode of the photoelectric conversion element 333 of the light reception unit 330. Furthermore, the drain of the LG transistor 411 is connected to, for example, a source of the LG transistor 413 and the gate of the amplification transistor 412. A drain of the LG transistor 413 is connected to the power supply terminal VDD, for example.

Furthermore, for example, a source of the amplification transistor 414 is connected to a gate of the LG transistor 411 and the drain of the amplification transistor 412. A drain of the amplification transistor 414 is connected to the power supply terminal VDD via the constant current circuit 415, for example.

A loop-shaped source follower circuit is formed by a connection relationship illustrated in FIG. 3 or 5. Therefore, the photocurrent from the light reception unit 330 is converted into a voltage signal of a logarithmic value according to the charge amount thereof. Note that each of the LG transistors 411 and 413 and the amplification transistors 412 and 414 may include, for example, an NMOS transistor.

1.4.2 Configuration Example of Subtractor and Quantizer

Figure 6:
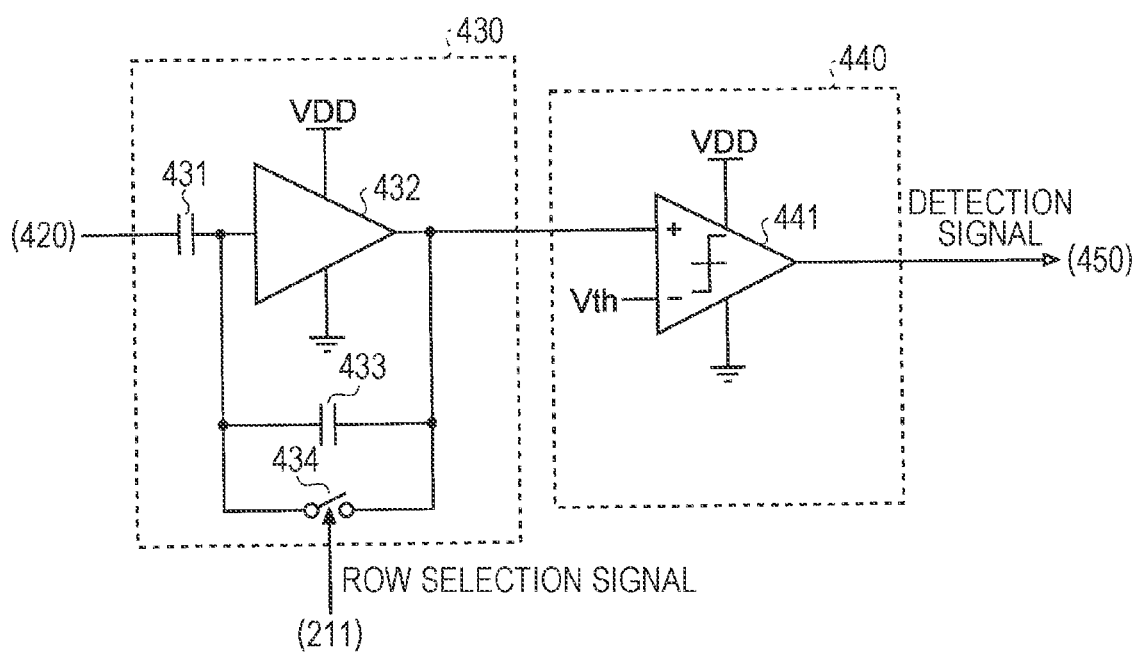
FIG. 6 is a circuit diagram illustrating a schematic configuration example of a subtractor and a quantizer according to the first embodiment.

FIG. 6 is a circuit diagram illustrating a schematic configuration example of the subtractor and the quantizer according to the first embodiment. As illustrated in FIG. 6, the subtractor 430 is provided with capacitors 431 and 433, an inverter 432, and a switch 434. Furthermore, the quantizer 440 is provided with a comparator 441.

One end of the capacitor 431 is connected to an output terminal of the buffer 420 and the other end thereof is connected to an input terminal of the inverter 432. The capacitor 433 is connected in parallel with the inverter 432. The switch 434 opens/closes a path connecting both the ends of the capacitor 433 according to the row drive signal.

The inverter 432 inverts the voltage signal input via the capacitor 431. The inverter 432 outputs the inverted signal to a non-inverting input terminal (+) of the comparator 441.

When the switch 434 is turned on, a voltage signal Vinit is input to a side of the buffer 420 of the capacitor 431. Furthermore, the opposite side becomes a virtual grounding terminal. Potential of this virtual grounding terminal is set to zero for convenience. At that time, potential Qinit accumulated in the capacitor 431 is expressed by following expression (1) when capacitance of the capacitor 431 is set to C1. In contrast, since both the ends of the capacitor 433 are short-circuited, an accumulated charge thereof is zero.

$$Q\text{init} = C1 \times V\text{init} \tag{1}$$

Next, considering a case where the switch 434 is turned off and the voltage on the side of the buffer 420 of the capacitor 431 changes to Vafter, a charge Qafter accumulated in the capacitor 431 is expressed by following expression (2).

$$Q\text{after} = C1 \times V\text{after} \tag{2}$$

In contrast, a charge Q2 accumulated in the capacitor 433 is expressed by following expression (3) when an output voltage is set to Vout.

$$Q2 = -C2 \times V\text{out} \tag{3}$$

At that time, a total charge amount of the capacitors 431 and 433 does not change, so that following expression (4) holds.

$$Q\text{init} = Q\text{after} + Q2 \tag{4}$$

By substituting expressions (1) to (3) into expression (4) and transforming, following expression (5) is obtained.

$$V\text{out} = -(C1/C2) \times (V\text{after} - V\text{init}) \tag{5}$$

Expression (5) expresses a subtraction operation of the voltage signal, and a gain of a subtraction result is C1/C2. Since it is generally desired to maximize the gain, it is preferable to design C1 larger and C2 smaller. In contrast, if C2 is too small, kTC noise increases and a noise characteristic might be deteriorated, so that a reduction in capacitance of C2 is limited to a range in which the noise may be allowed. Furthermore, since the address event detection unit 400 including the subtractor 430 is mounted for each unit pixel, there is a limitation in area in the capacitance C1 and the capacitance C2. In consideration of them, values of the capacitance C1 and the capacitance C2 are determined.

The comparator 441 compares the voltage signal from the subtractor 430 with a predetermined threshold voltage Vth applied to an inverting input terminal (−). The comparator 441 outputs a signal indicating a comparison result to the transfer unit 450 as the detection signal.

Furthermore, a gain A of an entire address event detection unit 400 described above is expressed by following expression (6) when a conversion gain of the current-voltage conversion unit 410 is set to $CG_{log}$ and a gain of the buffer 420 is set to '1'.

[Mathematical Expression 1]

$$A = \frac{CG_{log} \cdot C1}{C2} \sum_{n=1}^{N} i_{photo\_n} \quad (6)$$

In expression (6), $i_{photo\_n}$ represents a photocurrent of an n-th unit pixel, and its unit is, for example, ampere (A). N represents the number of unit pixels 310 in the pixel block and is '1' in this embodiment.

1.5 Application Example to Mobile Body

The state detection device 1 described above may be applied to various products. For example, this may be mounted on any type of mobile body such as an automobile, an electric automobile, a hybrid electric automobile, a motorcycle, a bicycle, a personal mobility, an airplane, a drone, a ship, and a robot.

Figure 7:
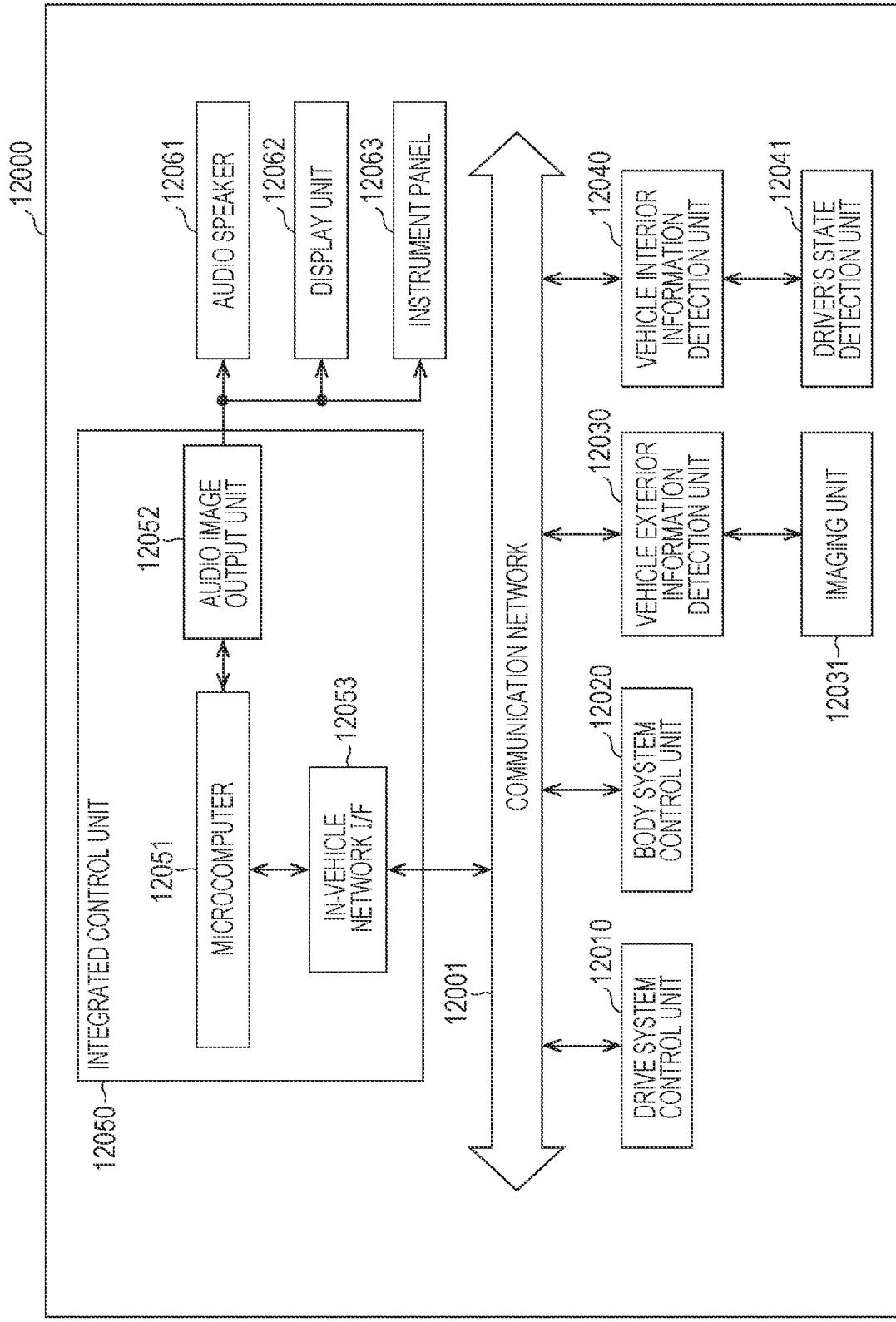
FIG. 7 is a block diagram illustrating a schematic configuration example of a vehicle control system that is an example of a mobile body control system according to the first embodiment.

FIG. 7 is a block diagram illustrating a schematic configuration example of a vehicle control system that is an example of a mobile body control system according to the first embodiment. As illustrated in FIG. 7, a vehicle control system 12000 is provided with a plurality of electronic control units connected to one another via a communication network 12001. In the example illustrated in FIG. 7, the vehicle control system 12000 is provided with a drive system control unit 12010, a body system control unit 12020, a vehicle exterior information detection unit 12030, a vehicle interior information detection unit 12040, and an integrated control unit 12050. Furthermore, a microcomputer 12051, an audio image output unit 12052, and an in-vehicle network interface (I/F) 12053 are illustrated as functional configurations of the integrated control unit 12050.

The drive system control unit 12010 controls an operation of a device related to a drive system of a vehicle according to various programs. For example, the drive system control unit 12010 serves as a control device of a driving force generating device for generating driving force of the vehicle such as an internal combustion engine or a driving motor, a driving force transmitting mechanism for transmitting the driving force to wheels, a steering mechanism for adjusting a rudder angle of the vehicle, a braking device for generating braking force of the vehicle and the like.

The body system control unit 12020 controls operations of various devices mounted on a vehicle body according to the various programs. For example, the body system control unit 12020 serves as a control device of a keyless entry system, a smart key system, a power window device, or various lights such as a headlight, a backing light, a brake light, a blinker, or a fog light. In this case, a radio wave transmitted from a portable device that substitutes for a key or signals of various switches may be input to the body system control unit 12020. The body system control unit 12020 receives an input of the radio wave or signals and controls a door locking device, a power window device, the lights and the like of the vehicle.

The vehicle exterior information detection unit 12030 detects information outside the vehicle equipped with the vehicle control system 12000. For example, an imaging unit 12031 is connected to the vehicle exterior information detection unit 12030. The vehicle exterior information detection unit 12030 allows the imaging unit 12031 to obtain information outside the vehicle and receives obtained data. The vehicle exterior information detection unit 12030 may perform detection processing of objects such as a person, a vehicle, an obstacle, a sign, or a character on a road surface or distance detection processing on the basis of the received data.

The imaging unit 12031 may be an image sensor that outputs an electric signal as an image, or may be a ranging sensor that outputs the same as ranging information. Furthermore, the light received by the imaging unit 12031 may be visible light or invisible light such as infrared light.

The vehicle interior information detection unit 12040 detects information inside the vehicle. The vehicle interior information detection unit 12040 is connected to, for example, a driver's state detection unit 12041 that detects a state of a driver. In this embodiment, the above-described DVS 200 (or the DVS 200 and the image sensor 14) is used for the driver's state detection unit 12041. In this case, the vehicle interior information detection unit 12040 connected to the driver's state detection unit 12041 and/or the microcomputer 12051 connected thereto via the communication network 12001 form the motion detection unit 12, the object detection unit 15, the motion vector estimation unit 16, and the action pattern determination unit 17 in the state detection device 1.

Figure 8:
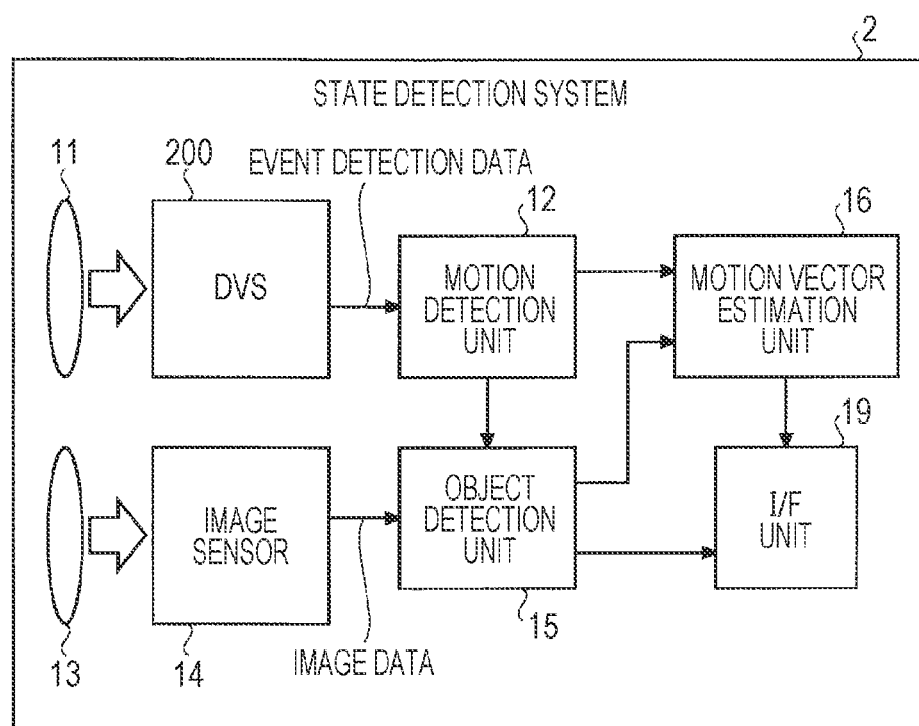
FIG. 8 is a block diagram illustrating another schematic configuration example of a state detection device (system) according to the first embodiment.

For example, it is also possible to provide the motion detection unit 12, the object detection unit 15, and the motion vector estimation unit 16 in the state detection device 1 separately from the vehicle interior information detection unit 12040 and the microcomputer 12051, and realize the action pattern determination unit 17 by the vehicle interior information detection unit 12040 and/or the microcomputer 12051 as in the state detection device 2 illustrated in FIG. 8.

Alternatively, the motion detection unit 12, the object detection unit 15, the motion vector estimation unit 16, and the action pattern determination unit 17 may have configurations different from those of the vehicle interior information detection unit 12040 and/or the microcomputer 12051.

The vehicle interior information detection unit 12040 may calculate a fatigue level or a concentration level of the driver or may determine whether or not the driver is dozing on the basis of detection information input from the driver's state detection unit 12041.

The microcomputer 12051 may perform an arithmetic operation of a control target value of the driving force generating device, the steering mechanism, or the braking device on the basis of the information inside and outside the vehicle obtained by the vehicle interior information detection unit 12040 or the vehicle exterior information detection unit 12030, and output a control instruction to the drive system control unit 12010. For example, the microcomputer 12051 may perform cooperative control for realizing functions of advanced driver assistance system (ADAS) including collision avoidance or impact attenuation of the vehicle, following travel based on an inter-vehicular distance, vehicle speed maintaining travel, vehicle collision warning, vehicle lane departure warning or the like.

Furthermore, the microcomputer 12051 may perform the cooperative control for realizing automatic driving and the like to autonomously travel independent from the operation of the driver by controlling the driving force generating device, the steering mechanism, the braking device or the like on the basis of the information around the vehicle obtained by the vehicle exterior information detection unit 12030 or the vehicle interior information detection unit 12040.

Furthermore, the microcomputer 12051 may output the control instruction to the body system control unit 12020 on the basis of the information outside the vehicle obtained by the vehicle exterior information detection unit 12030. For example, the microcomputer 12051 may perform the cooperative control for realizing glare protection such as controlling the headlight according to a position of a preceding vehicle or an oncoming vehicle detected by the vehicle exterior information detection unit 12030 to switch a high beam to a low beam.

The audio image output unit 12052 transmits at least one of audio or image output signal to an output device capable of visually or audibly notifying an occupant of the vehicle or the outside the vehicle of the information. In the example in FIG. 7, as the output device, an audio speaker 12061, a display unit 12062, and an instrument panel 12063 are illustrated. The display unit 12062 may include at least one of an on-board display or a head-up display, for example.

1.6 Arrangement Example of Imaging Unit

Figure 9:
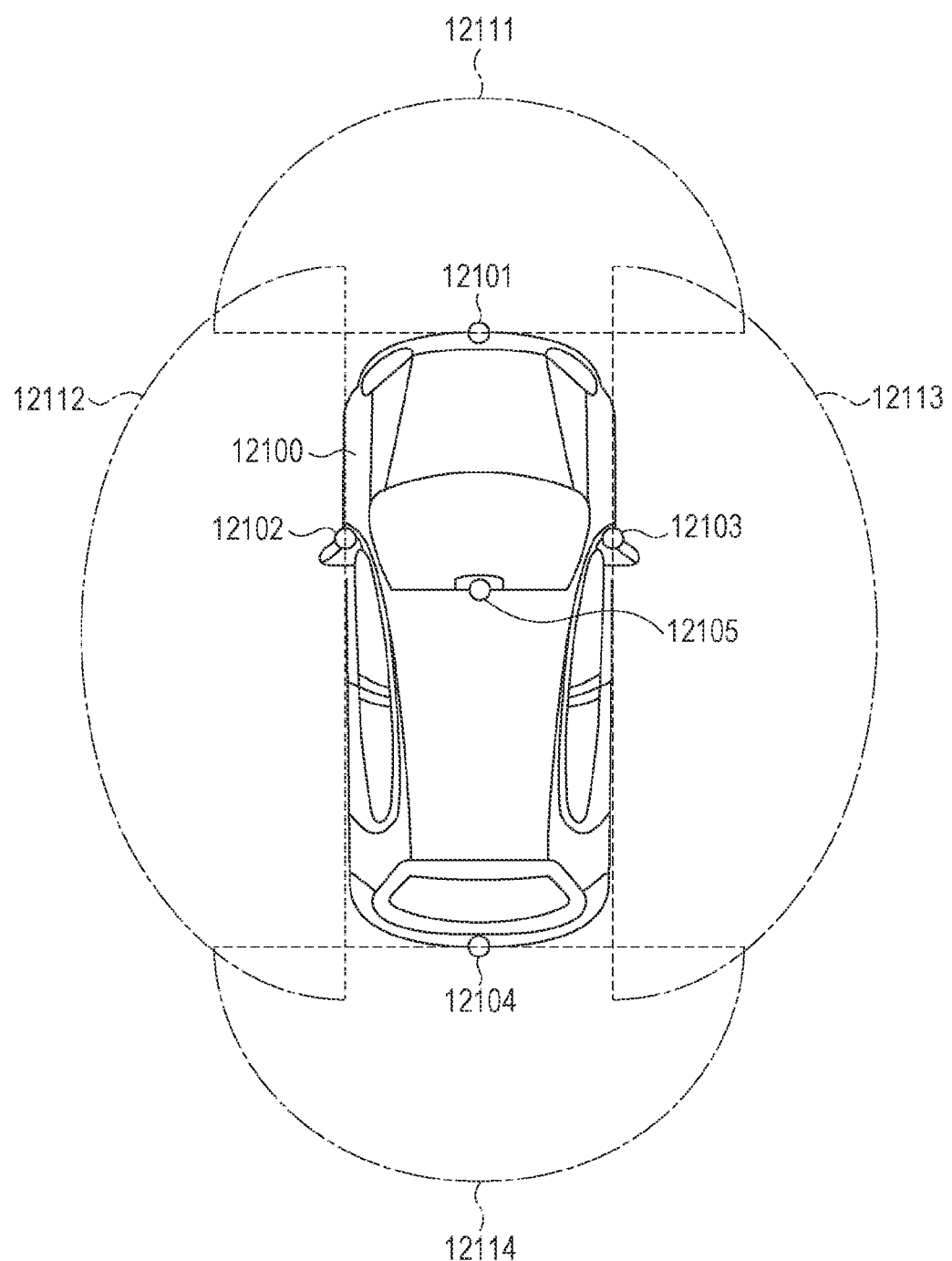
FIG. 9 is a view illustrating an example of an installation position of an imaging unit according to the first embodiment with respect to a vehicle.

FIG. 9 is a view illustrating an example of an installation position of the imaging unit according to the first embodiment with respect to the vehicle. In FIG. 9, as the imaging unit 12031, a total of five imaging units including the imaging units 12101, 12102, 12103, 12104, and 12105 are provided for the vehicle 12100.

The imaging units 12101, 12102, 12103, 12104, and 12105 are provided in positions such as, for example, a front nose, a side mirror, a rear bumper, a rear door, and an upper portion of a windshield in a vehicle interior of the vehicle 12100. The imaging unit 12101 provided on the front nose and the imaging unit 12105 provided in the upper portion of the windshield in the vehicle interior principally obtain images of the area in front of the vehicle 12100. The imaging units 12102 and 12103 provided on the side mirrors principally obtain images of the sides of the vehicle 12100. The imaging unit 12104 provided on the rear bumper or the rear door principally obtains an image of an area behind the vehicle 12100. The imaging unit 12105 provided in the upper portion of the windshield in the vehicle interior is principally used for detecting a preceding vehicle, a pedestrian, an obstacle, a traffic light, a traffic sign, a lane or the like.

Furthermore, in FIG. 9, an example of imaging ranges of the imaging units 12101 to 12104 is illustrated. An imaging range 12111 indicates the imaging range of the imaging unit 12101 provided on the front nose, imaging ranges 12112 and 12113 indicate the imaging ranges of the imaging units 12102 and 12103 provided on the side mirrors, and an imaging range 12114 indicates the imaging range of the imaging unit 12104 provided on the rear bumper or the rear door. For example, image data imaged by the imaging units 12101 to 12104 are superimposed, so that an overlooking image of the vehicle 12100 as seen from above is obtained.

At least one of the imaging units 12101 to 12104 may have a function of obtaining distance information. For example, at least one of the imaging units 12101 to 12104 may be a stereo camera including a plurality of imaging elements, or may be an imaging element including pixels for phase difference detection.

For example, the microcomputer 12051 (refer to FIG. 7) may extract especially a closest solid object on a traveling path of the vehicle 12100, the solid object traveling at a predetermined speed (for example, 0 km/h or higher) in a direction substantially the same as that of the vehicle 12100 as the preceding vehicle by obtaining a distance to each solid object in the imaging ranges 12111 to 12114 and a change in time of the distance (relative speed relative to the vehicle 12100) on the basis of the distance information obtained from the imaging units 12101 to 12104. Moreover, the microcomputer 12051 may set the inter-vehicular distance to be secured in advance from the preceding vehicle, and may perform automatic brake control (including following stop control), automatic acceleration control (including following start control) and the like. In this manner, it is possible to perform the cooperative control for realizing the automatic driving and the like to autonomously travel independent from the operation of the driver.

For example, the microcomputer 12051 may extract solid object data regarding the solid object while sorting the same into a motorcycle, a standard vehicle, a large-sized vehicle, a pedestrian, and other solid objects such as a utility pole on the basis of the distance information obtained from the imaging units 12101 to 12104 and use for automatically avoiding obstacles. For example, the microcomputer 12051 discriminates the obstacles around the vehicle 12100 into an obstacle visible to a driver of the vehicle 12100 and an obstacle difficult to see. Then, the microcomputer 12051 determines a collision risk indicating a degree of risk of collision with each obstacle, and when the collision risk is equal to or higher than a set value and there is a possibility of collision, this may perform driving assistance for avoiding the collision by outputting an alarm to the driver via the audio speaker 12061 and the display unit 12062 or performing forced deceleration or avoidance steering via the drive system control unit 12010.

At least one of the imaging units 12101 to 12104 may be an infrared camera that detects infrared light. For example, the microcomputer 12051 may recognize a pedestrian by determining whether or not there is a pedestrian in the images taken by the imaging units 12101 to 12104. Such pedestrian recognition is carried out, for example, by a procedure of extracting feature points in the images taken by the imaging units 12101 to 12104 as the infrared cameras, and a procedure of performing pattern matching processing on a series of feature points indicating an outline of an object to discriminate whether or not this is a pedestrian. When the microcomputer 12051 determines that there is the pedestrian in the images taken by the imaging units 12101 to 12104 and recognizes the pedestrian, the audio image output unit 12052 controls the display unit 12062 to superimpose a rectangular contour for emphasis on the recognized pedestrian to display. Furthermore, the audio image output unit 12052 may control the display unit 12062 to display an icon and the like indicating the pedestrian in a desired position.

1.7 Arrangement Example of Driver's State Detection Unit (DVS)

Figure 10:
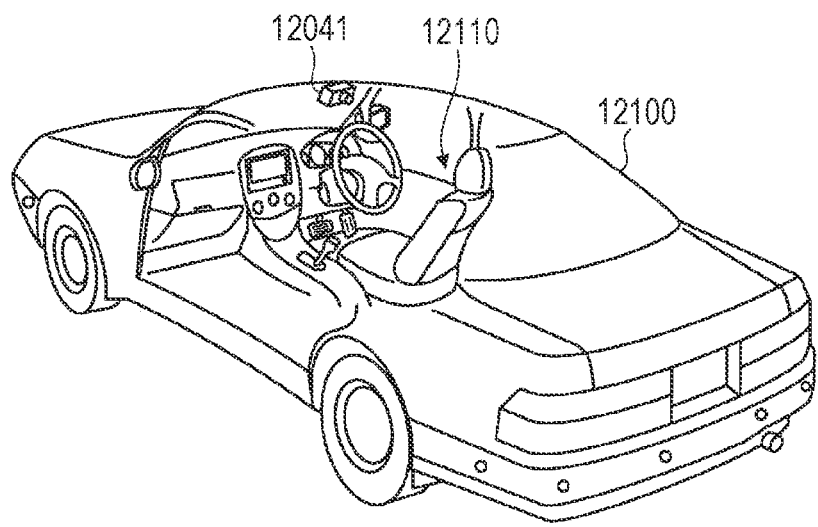
FIG. 10 is a view illustrating an example of an installation position of a driver's state detection unit according to the first embodiment with respect to the vehicle.
Figure 11:
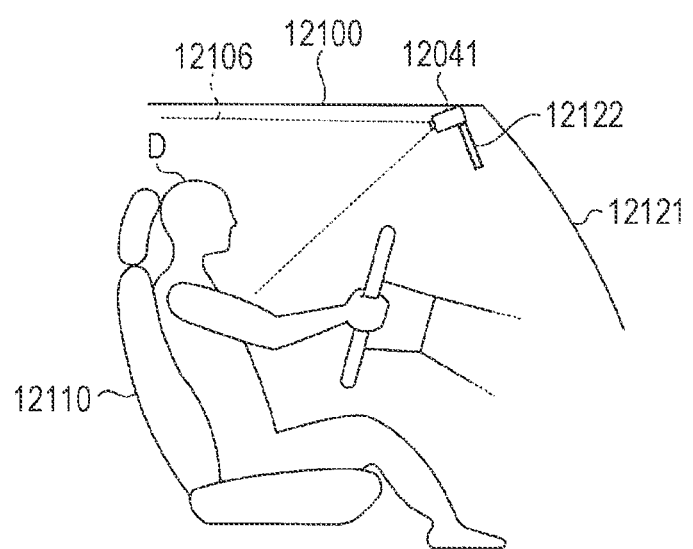
FIG. 11 is a view for explaining an angle of view of the driver's state detection unit according to the first embodiment.

FIG. 10 is a view illustrating an example of an installation position of the driver's state detection unit according to the first embodiment with respect to the vehicle. FIG. 11 is a view for explaining an angle of view of the driver's state detection unit according to the first embodiment.

As illustrated in FIGS. 10 and 11, the driver's state detection unit 12041 is provided in a position facing a driver seat 12110 inside the vehicle 12100, the position in which at least a face of a driver D gets into an angle of view 12106. In the example illustrated in FIGS. 10 and 11, this is provided on an upper edge of a rearview mirror 12122 provided at the center on an upper side of a windshield 12121 on the vehicle interior side, the position in which the rearview mirror 12122 is not hidden from the driver D. However, the position is not limited to this position, and may be variously changed; for example, such as a position on a lower edge or a side edge of the rearview mirror 12122, the position in which the rearview mirror 12122 is not hidden from the driver D, or a position on the vehicle interior side of the windshield 12121 above and in front of the driver seat 12110, the position in which an eyesight of the driver D toward the vehicle outside is not obstructed.

1.8 State Detection Operation Example

Figure 12:
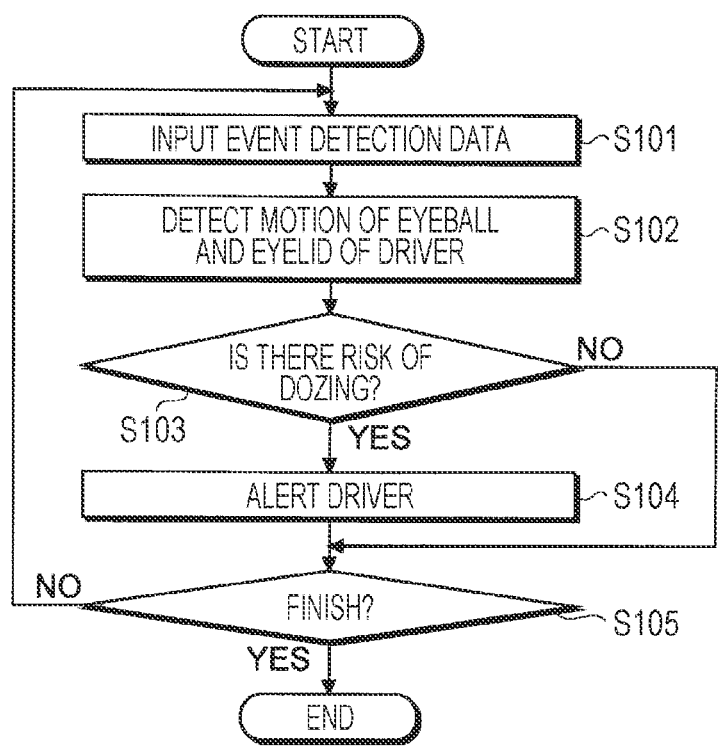
FIG. 12 is a flowchart illustrating an example of a state detection operation executed by the state detection device according to the first embodiment.

Next, an operation example of the state detection device according to the first embodiment is described. FIG. 12 is a flowchart illustrating an example of a state detection operation executed by the state detection device according to the first embodiment.

As illustrated in FIG. 12, in this operation, first, the event detection data is input from the DVS 200 to the motion detection unit 12 (and the object detection unit 15) (step S101). At that time, the image data may also be input from the image sensor 14 to the motion detection unit 12 (and the object detection unit 15). Note that each of the DVS 200 and the image sensor 14 is installed, for example, such that the face of the driver D seated on the driver seat 12110 gets into the angle of view thereof.

In contrast, the motion detection unit 12, the object detection unit 15, and the motion vector estimation unit 16 detect an eyeball and an eyelid of the driver D as objects from the input event detection data (and image data), then detect motion of the detected eyeball and eyelid (step S102). Information regarding the detected motion of the eyeball and eyelid is input to the action pattern determination unit 17.

The action pattern determination unit 17 detects the state of the driver D from the input motion of the eyeball and eyelid, and determines whether or not the driver D is in danger of dozing from a detection result thereof (step S103). For example, the action pattern determination unit 17 estimates a degree of wakefulness (hereinafter, referred to as a level of wakefulness) of the driver D from an opening amount of the eyelid and an opening/closing speed of the eyelid, and determines whether or not the driver D is in danger of dozing on the basis of the estimated level of wakefulness.

Figure 13:
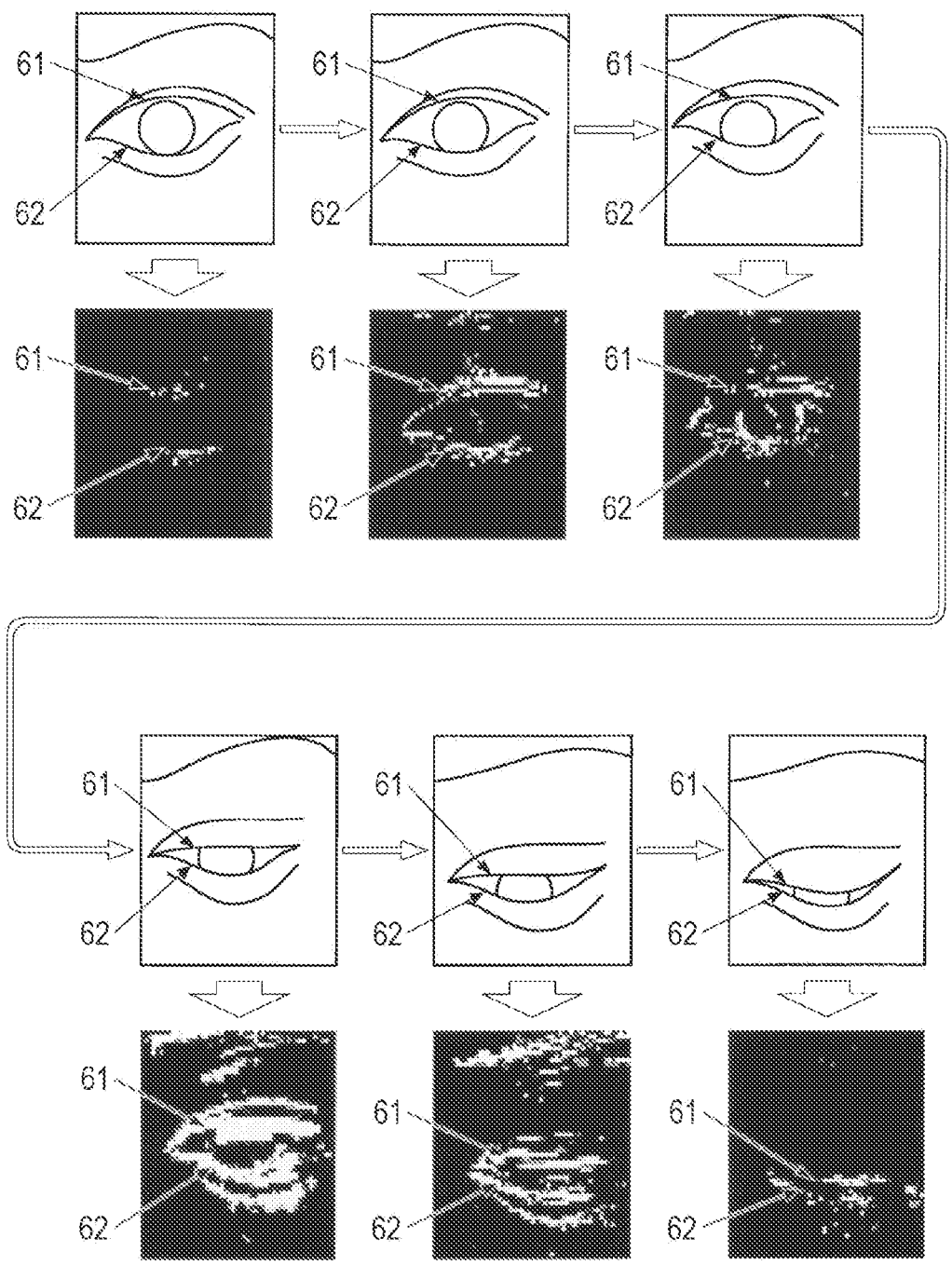
FIG. 13 is a view illustrating motion of an eyelid when blinking.
Figure 14:
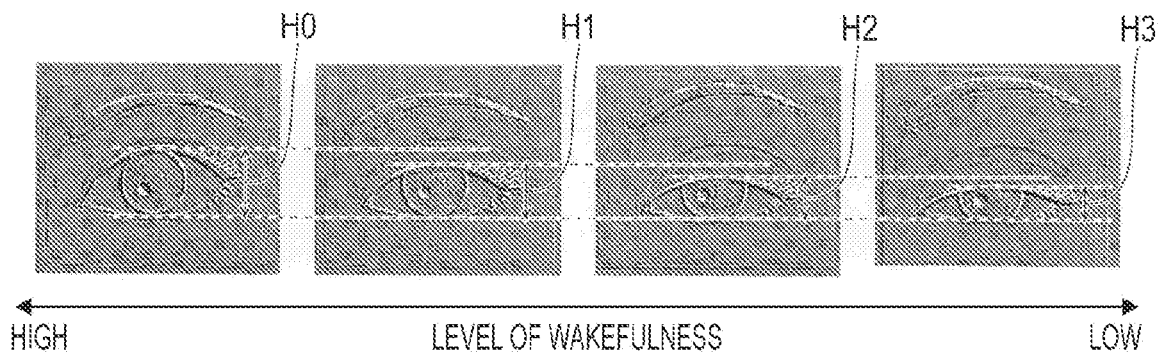
FIG. 14 is a view illustrating a relationship between a level of wakefulness and an eyelid state (opening amount).

Here, a difference between the motion of the eyelid when the level of wakefulness is low, that is, sleepiness is strong and the motion of the eyelid when blinking is described. FIG. 13 is a view illustrating the motion of the eyelid when blinking, and FIG. 14 is a view illustrating a relationship between the level of wakefulness and an eyelid state (opening amount). Note that, in FIG. 13, a schematic diagram of an actually imaged eye is illustrated in an upper part, and a frame image based on the event detection data obtained by observing the actual eye with the DVS 200 is illustrated in a lower part.

As illustrated in FIG. 13, in normal blink, an upper eyelid 61 and a lower eyelid 62 quickly open and close. Therefore, in a case where this blink is observed by the DVS 200, the frame image of the entire eye including the upper eyelid 61 and the lower eyelid 62 is obtained.

In contrast, as illustrated in FIG. 14, an eye opening amount in a state of not blinking (referred to as normal time) changes according to the level of wakefulness of the person (for example, the driver D). For example, an eye opening amount H0 at the normal time when the level of wakefulness is high is large, and the eye opening amount at the normal time decreases as the level of wakefulness decreases (H0→H1→H2→H3).

Therefore, at step S103, for example, the action pattern determination unit 17 may obtain a motion vector of the eyelid within a predetermined time (for example, 0.5 seconds), an average value of the eye opening amount and the like, estimate whether the driver D blinks or the level of wakefulness is low (the sleepiness is strong) on the basis of these values, and determine whether or not the driver D is in danger of dozing.

In a case of determining that the driver D is not in danger of dozing (NO at step S103), the action pattern determination unit 17 proceeds to step S105. In contrast, in a case of determining that the driver D is in danger of dozing (YES at step S103), the action pattern determination unit 17 drives the audio image output unit 12052 in FIG. 7, for example, to issue an alert for awakening the driver D from the audio speaker 12061 (step S104), and proceeds to step S105. At that time, the action pattern determination unit 17 may display an alert including a video, a color and the like for awakening the driver D on the display unit 12062.

At step S105, the action pattern determination unit 17 determines whether or not to finish this operation, and in a case of finishing (YES at step S105), this finishes this operation. In contrast, in a case of continuing (NO at step S105), the action pattern determination unit 17 returns to step S101 and executes the subsequent operation.

1.9 Action and Effect

As described above, according to this embodiment, the DVS 200 is used as the sensor for detecting the state of the driver, the state of the driver may be detected more quickly. Furthermore, in this embodiment, the state of the driver is detected using the event detection data of a smaller data amount instead of the image data obtained by the normal image sensor, so that it is also possible to reduce the power consumption at the time of state detection.

2. Second Embodiment

Next, a second embodiment is described in detail with reference to the drawings. Note that, in the following description, the configuration and operation similar to those of the first embodiment are cited, and the description thereof is not repeated.

In recent years, there is a technology of mounting an image sensor that images an area behind a vehicle on a rear end of the vehicle and installing a rearview mirror type monitor (hereinafter, referred to as an electronic mirror or a display unit) instead of a rearview mirror, and reproducing a video imaged by the image sensor at the rear end in real time on the electronic mirror in the vehicle.

Figure 15:
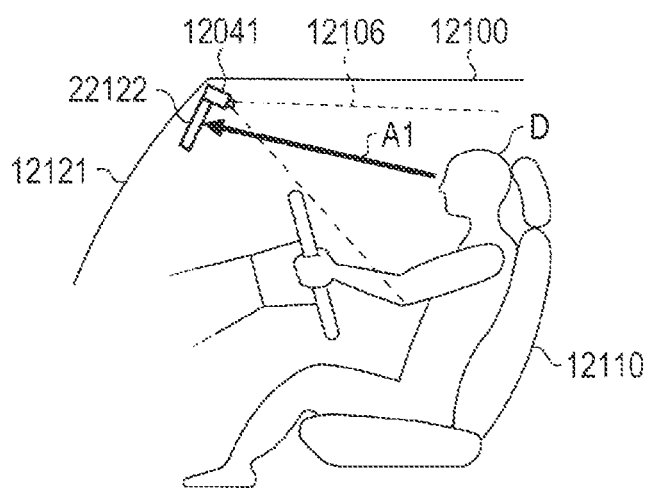
FIG. 15 is a view illustrating a case where an eye line of a driver is in a direction to an electronic mirror.
Figure 16:
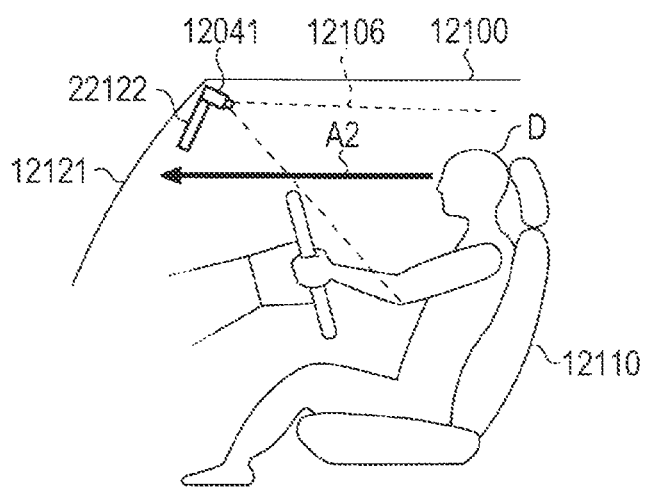
FIG. 16 is a view illustrating a case where the eye line of the driver is not in the direction to the electronic mirror.

However, reproducing the video of the area behind the vehicle on the electronic mirror when a driver does not look at the electronic mirror might cause an increase in power consumption. Therefore, in this embodiment, an electronic mirror 22122 is turned on in a case where a direction of eye line A1 of a driver D is in a direction to the electronic mirror 22122 as illustrated in FIG. 15, and the electronic mirror is turned off in a case where a direction of eye line A2 of the driver D is not in the direction to the electronic mirror, for example, in a case where the driver D looks at an area in front of the vehicle through a windshield 12121 as illustrated in FIG. 16, thereby suppressing an increase in power consumption.

Note that the image sensor that images the area behind the vehicle at the rear end of the vehicle may be, for example, the imaging unit 12104 described with reference to FIG. 9 in the first embodiment.

Furthermore, a configuration example of a state detection device (or system) according to this embodiment may be similar to, for example, that of the state detection device 1 exemplified in the first embodiment.

2.1 State Detection Operation Example

Figure 17:
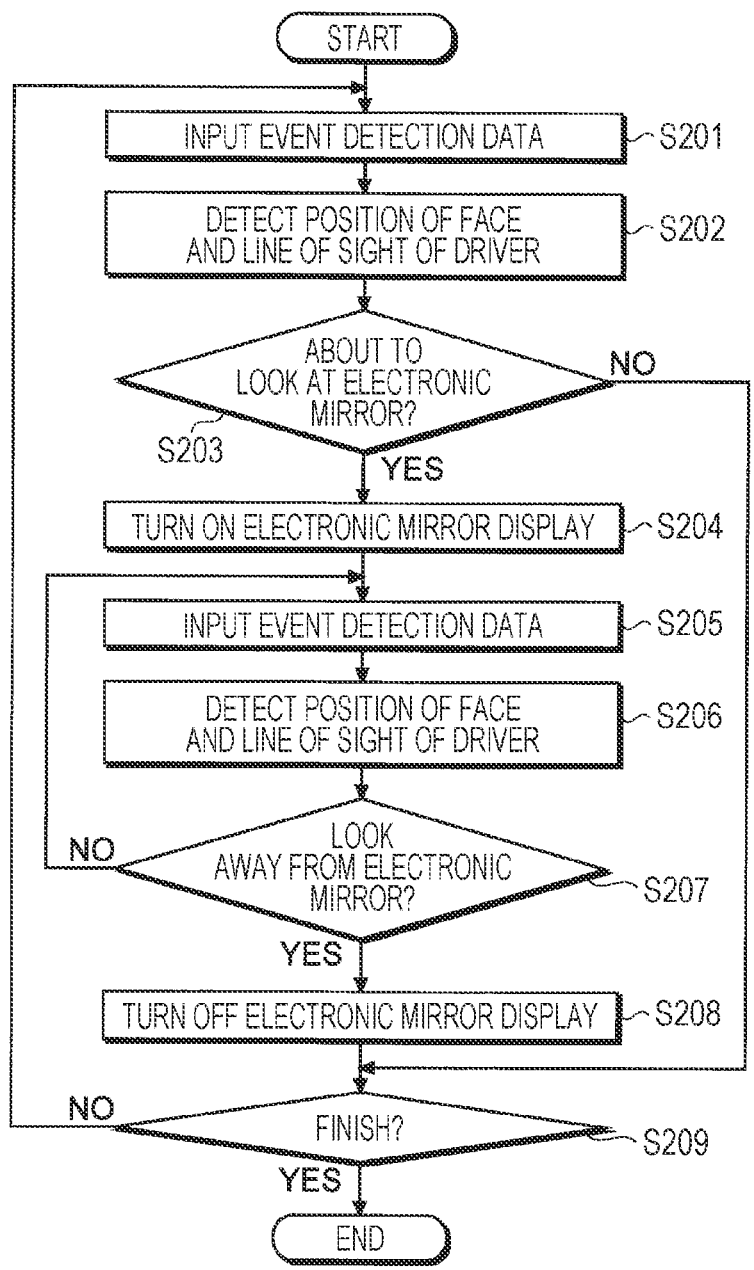
FIG. 17 is a flowchart illustrating an example of a state detection operation executed by a state detection device according to a second embodiment.

FIG. 17 is a flowchart illustrating an example of a state detection operation executed by the state detection device according to the second embodiment.

As illustrated in FIG. 17, in this operation, first, a position of a face and a direction of a line of sight of the driver D seated on a driver seat 12110 are detected by an operation similar to the operation described at steps S101 to S102 in FIG. 12 in the first embodiment (steps S201 to S202). Information regarding the detected position of the face and direction of the line of sight is input to an action pattern determination unit 17.

The action pattern determination unit 17 determines whether or not there is the electronic mirror 22122 corresponding to a rearview mirror 12122 in the direction of the line of sight of the driver D, that is, whether or not the driver D looks at or is about to look at the electronic mirror 22122 from the input position of the face and direction of the line of sight (step S203).

In a case where the driver D does not look at or is not about to look at the electronic mirror 22122 (NO at step S203), the action pattern determination unit 17 proceeds to step S209. In contrast, in a case where the driver D looks at or is about to look at the electronic mirror 22122 (YES at step S203), the action pattern determination unit 17 turns on display of the electronic mirror 22122 (step S204). Therefore, the electronic mirror 22122 displays the video of the area behind the vehicle imaged by the imaging unit 12104 installed at the rear end of the vehicle 12100.

When the display of the electronic mirror 22122 is turned on in this manner, next, the position of the face and the direction of the line of sight of the driver D seated on the driver seat 12110 are detected by an operation similar to the operation described at steps S101 to S102 in FIG. 12 in the first embodiment (steps S205 to S206). Then, this time, the action pattern determination unit 17 determines whether or not the driver D looks away from the electronic mirror 22122 (step S207). Note that the information regarding the position of the face and the direction of the line of sight detected at step S206 is input to the action pattern determination unit 17.

In a case where the driver D does not look away from the electronic mirror 22122 (NO at step S207), this operation returns to step S205 to continue displaying the video of the area behind the vehicle on the electronic mirror 22122. In contrast, in a case where the driver D looks away from the electronic mirror 22122 (YES at step S207), the action pattern determination unit 17 turns off the display of the electronic mirror 22122 (step S208) and proceeds to step S209. Therefore, the power consumption by the electronic mirror 22122 when this is not used is reduced.

At step S209, the action pattern determination unit 17 determines whether or not to finish this operation, and in a case of finishing (YES at step S209), this finishes this operation. In contrast, in a case of continuing (NO at step S209), the action pattern determination unit 17 returns to step S201 and executes the subsequent operation.

By the above-described operation, in this embodiment, it becomes possible to reduce the power consumption by the electronic mirror 22122 in a period in which the driver D does not look at the electronic mirror 22122.

2.2 Action and Effect

Other configurations, operations, and effects may be similar to those of the above-described embodiment, so that the detailed description thereof is herein omitted.

2.3 Variation

Furthermore, the display of the electronic mirror 22122 may be automatically turned on/off not only in a case where the driver D actively looks at the electronic mirror 22122 but also, for example, in a case of calling driver D's attention to the electronic mirror 22122, that is, in a case of calling driver D's attention to the area behind the vehicle. For example, in a case where an inter-vehicular distance to a following vehicle is short and there is a risk of collision, and in a case where the driver D is not aware of the risk, it is possible to call the driver D's attention to the electronic mirror 22122 by turning on the display of the electronic mirror 22122.

Figure 18:
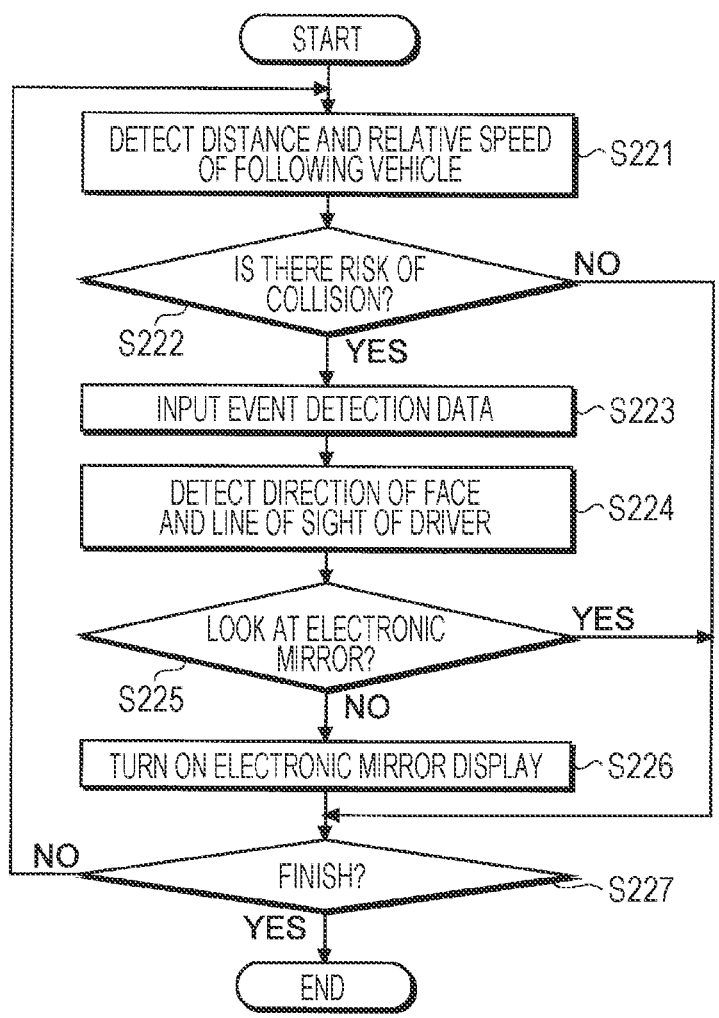
FIG. 18 is a flowchart illustrating an example of a state detection operation executed by a state detection device according to a variation of the second embodiment.

FIG. 18 is a flowchart illustrating an example of a state detection operation executed by a state detection device according to this variation.

As illustrated in FIG. 18, in this operation, an action pattern determination unit 17 or a microcomputer 12051 detects the inter-vehicular distance to the following vehicle, a relative speed relative to the following vehicle and the like on the basis of image data or a ranging result obtained by an imaging unit 12104 arranged at a rear end of a vehicle 12100, for example (step S221). Then, the action pattern determination unit 17 or the microcomputer 12051 determines whether or not there is a possibility of collision with the following vehicle from the inter-vehicular distance to the following vehicle, the relative speed relative to the following vehicle and the like that are detected (step S222). Note that it is possible to determine whether or not the inter-vehicular distance to the following vehicle becomes shorter or is likely to be shorter than a certain threshold, whether or not a driver D should pay attention to the area behind the vehicle 12100 and the like in addition to whether or not there is a possibility of collision with the following vehicle.

In a case where there is no possibility of collision with the following vehicle and the like (NO at step S222), this operation proceeds to step S227. In contrast, in a case where there is a possibility of collision with the following vehicle and the like (YES at step S222), a position of a face and a direction of a line of sight of the driver D seated on a driver seat 12110 are detected by an operation similar to the operation described at steps S101 to S102 in FIG. 12 in the first embodiment (steps S223 to S224). Then, the action pattern determination unit 17 determines whether or not the driver D looks at the electronic mirror 22122, that is, whether or not the driver D is aware of the possibility of collision with the following vehicle and the like (step S225).

In a case where the driver D looks at the electronic mirror 22122 (YES at step S225), this operation proceeds to step S227. In contrast, in a case where the driver D does not look at the electronic mirror 22122 (NO at step S225), the action pattern determination unit 17 turns on display of the electronic mirror 22122 (step S226). Therefore, the electronic mirror 22122 displays the video of the area behind the vehicle imaged by the imaging unit 12104 installed at the rear end of the vehicle 12100.

As described above, the display of electronic mirror 22122 is automatically turned on, so that the driver D is urged to pay attention to the electronic mirror 22122. At that time, for example, the action pattern determination unit 17 may drive an audio image output unit 12052 in FIG. 7 to issue an alert for calling attention to the electronic mirror 22122 or the following vehicle from an audio speaker 12061, or may display an alert for calling attention to the electronic mirror 22122 or the following vehicle on a display unit 12062.

At step S227, the action pattern determination unit 17 determines whether or not to finish this operation, and in a case of finishing (YES at step S227), this finishes this operation. In contrast, in a case of continuing (NO at step S227), the action pattern determination unit 17 returns to step S221 and executes the subsequent operation.

Although the embodiments of the present disclosure are described above, the technical scope of the present disclosure is not limited to the above-described embodiments, and various modifications may be made without departing from the gist of the present disclosure. Furthermore, the components of different embodiments and variations may be appropriately combined.

Furthermore, the effects described in each embodiment of the present specification are illustrative only and are not limitative; there may also be another effect.

Note that the present technology may also have following configurations.

(1)

A state detection device provided with:
  a first solid-state imaging device provided with a plurality of pixels arranged in a matrix, the first solid-state imaging device that detects, according to a light amount incident on each of the pixels, occurrence of an event in each of the pixels; and
  a state detection unit that detects a state of a driver on the basis of the occurrence of the event detected by the first solid-state imaging device.

(2)

The state detection device according to (1) described above, in which
  the state detection unit detects at least one of motion of an eyeball, motion of an eyelid, a direction of a face, or a direction of a line of sight of the driver as the state of the driver.

(3)

The state detection device according to (1) or (2) described above, further provided with:
  an action pattern determination unit that determines an action pattern on the basis of the state of the driver detected by the state detection unit.

(4)

The state detection device according to (3) described above, in which
  the state detection unit detects at least one of motion of an eyeball or motion of an eyelid of the driver, and
  the action pattern determination unit estimates a degree of wakefulness of the driver on the basis of at least one of the motion of the eyeball or the motion of the eyelid, and determines the action pattern on the basis of the estimated degree of wakefulness.

(5)

The state detection device according to (4) described above, in which
  the action pattern determination unit determines the action pattern of outputting an alert for awakening the driver in a case where the estimated degree of wakefulness is low.

(6)

The state detection device according to (3) described above, further provided with:
  an imaging unit that images an area behind a vehicle; and
  a display unit that displays a video imaged by the imaging unit, in which
  the state detection unit detects at least one of a direction of a face or a direction of a line of sight of the driver, and
  the action pattern determination unit determines whether or not the driver looks at or is about to look at the display unit on the basis of at least one of the direction of the face or the direction of the line of sight, and determines the action pattern on the basis of a result of the determination.

(7)

The state detection device according to (6), in which
  the action pattern determination unit determines an action pattern of allowing the display unit to display the video in a case where the driver looks at or is about to look at the display unit, and determines an action pattern of turning off display of the display unit in a case where the driver does not look at or is not about to look at the display unit.

(8)

The state detection device according to (3) described above, further provided with:
  an imaging unit that images an area behind a vehicle;
  a sensor that detects at least one of an inter-vehicular distance to a following vehicle or a relative speed relative to the following vehicle; and
  a display unit that displays a video imaged by the imaging unit, in which
  the state detection unit detects at least one of a direction of a face and a direction of a line of sight of the driver, and
  the action pattern determination unit determines the action pattern on the basis of at least one of the inter-vehicular distance or the relative speed and at least one of the direction of the face or the direction of the line of sight.

(9)

The state detection device according to (8) described above, in which
  the action pattern determination unit determines whether or not there is a risk of collision with the following vehicle on the basis of at least one of the inter-vehicular distance or the relative speed, further determines whether or not the driver looks at or is about to look at the display unit on the basis of at least one of the direction of the face or the direction of the line of sight in a case where there is the risk of collision with the following vehicle, and determines an action pattern of allowing the display unit to display the video in a case where the driver does not look at or is not about to look at the display unit.

(10)

The state detection device according to any one of (1) to (9) described above, further provided with:
  a second solid-state imaging device that images a face of the driver, in which
  the state detection unit detects the state of the driver on the basis of the occurrence of the event detected by the first solid-state imaging device and image data obtained by the second solid-state imaging device.

(11)

A state detection system provided with:
  a first solid-state imaging device provided with a plurality of pixels arranged in a matrix, the first solid-state imaging device that detects, according to a light amount incident on each of the pixels, occurrence of an event in each of the pixels; and
  a state detection unit that detects a state of a driver on the basis of the occurrence of the event detected by the first solid-state imaging device.

(12)

A state detection method provided with:
  detecting a state of a driver on the basis of occurrence of an event detected by a solid-state imaging device provided with a plurality of pixels arranged in a matrix, the solid-state imaging device that detects, according to a light amount incident on each of the pixels, the occurrence of the event in each of the pixels.

REFERENCE SIGNS LIST 1, 2 State detection device (system)
11, 13 Imaging lens
12 Motion detection unit
14 Image sensor
15 Object detection unit
16 Motion vector estimation unit
17 Action pattern determination unit
18 Storage unit
19 I/F unit
200 DVS
210 Logic circuit
211 Drive circuit
212 Signal processing unit
213 Arbiter
300 Pixel array unit
330 Light reception unit
333 Photoelectric conversion element
400 Address event detection unit
410 Current-voltage conversion unit
411, 413 LG transistor
412, 414 Amplification transistor
415 Constant current circuit
420 Buffer
430 Subtractor
431, 433 Capacitor
432 Inverter
434 Switch
440 Quantizer
441 Comparator
450 Transfer unit
12000 Vehicle control system
12001 Communication network
12010 Drive system control unit
12020 Body system control unit
12030 Vehicle exterior information detection unit
12031, 12101 to 12105 Imaging unit
12040 Vehicle interior information detection unit
12041 Driver's state detection unit
12050 Integrated control unit
12051 Microcomputer
12052 Audio image output unit
12053 In-vehicle network I/F
12061 Audio speaker
12062 Display unit
12063 Instrument panel
12100 Vehicle
12106 Angle of view
12110 Driver sheet
12111 to 12114 Imaging range
12121 Windshield
12122 Rearview mirror
22122 Electronic mirror
A1, A2 Direction of eye line
D Driver

The invention claimed is:
1. A state detection device, comprising:
a first solid-state imaging device comprising a plurality of pixels, wherein each pixel of the plurality of pixels is configured to:
receive incident light; and
detect, based on an amount of the incident light, occurrence of an event in a corresponding pixel of the plurality of pixels;
a second solid-state imaging device configured to:
capture a face of a driver; and
obtain image data based on the captured face; and
a state detection unit configured to detect a state of the driver based on the occurrence of the event and the image data.
2. The state detection device according to claim 1, wherein the state detection unit is further configured to detect at least one of motion of an eyeball, motion of an eyelid, a direction of the face, or a direction of a line of sight of the driver as the state of the driver.
3. The state detection device according to claim 1, further comprising an action pattern determination unit configured to determine an action pattern based on the detected state of the driver.
4. The state detection device according to claim 3, wherein
the state detection unit is further configured to detect at least one of motion of an eyeball or motion of an eyelid of the driver, and
the action pattern determination unit is further configured to:
estimate a degree of wakefulness of the driver based on the at least one of the motion of the eyeball or the motion of the eyelid; and
determine the action pattern based on the estimated degree of wakefulness.
5. The state detection device according to claim 4, wherein the action pattern determination unit is further configured to determine the action pattern, to alert the driver, based on the estimated degree of wakefulness.
6. The state detection device according to claim 3, further comprising:
an imaging unit configured to image video of an area behind a vehicle; and
a display unit configured to display the video imaged by the imaging unit, wherein
the state detection unit is further configured to detect at least one of a direction of the face or a direction of a line of sight of the driver, and
the action pattern determination unit is further configured to:
determine that the driver looks at or is about to look, at the display unit, based on the at least one of the direction of the face or the direction of the line of sight; and
determine the action pattern based on the determination.
7. The state detection device according to claim 6, wherein the action pattern determination unit is further configured to:
determine the action pattern to allow the display unit to display the video in a case where the driver looks at or is about to look at the display unit; and
determine the action pattern to turn off the display unit in a case where the driver looks away or is about to look away from the display unit.
8. The state detection device according to claim 3, further comprising:
an imaging unit configured to image video of an area behind a vehicle;
a sensor configured to detect at least one of an inter-vehicular distance to a following vehicle or a relative speed relative to the following vehicle; and a display unit a configured to display the video imaged by the imaging unit, wherein
the state detection unit is configured to detect at least one of a direction of the face or a direction of a line of sight of the driver, and
the action pattern determination unit is further configured to determine the action pattern based on at least one of the inter-vehicular distance or the relative speed and at least one of the direction of the face or the direction of the line of sight.

9. The state detection device according to claim 8, wherein the action pattern determination unit is further configured to:
determine a risk of collision with the following vehicle based on at least one of the inter-vehicular distance or the relative speed;
determine that the driver looks at or is about to look, at the display unit, based on a basis of at least one of the direction of the face or the direction of the line of sight in a case where there is the risk of collision with the following vehicle; and
determine an action pattern to allow the display unit to display the video in a case where the driver looks away or is about to look away from the display unit.

10. A state detection system, comprising:
a first solid-state imaging device comprising a plurality of pixels, wherein each pixel of the plurality of pixels is configured to:
receive incident light; and
detect, based on an amount of the incident light occurrence of an event in a corresponding pixel of the plurality of pixels;
a second solid-state imaging device configured to:
capture a face of a driver; and
obtain image data based on the captured face; and
a state detection unit configured to detect a state of the driver on a based on the occurrence of the event and the image data.

11. A state detection method, comprising:
detecting a state of a driver based on occurrence of an event and image data, wherein
the occurrence of the event is detected by a first solid-state imaging device,
the image data is obtained by a second solid-state imaging device,
the first solid-state imaging device comprises a plurality of pixels, wherein each pixel of the plurality of pixels is configured to:
receive incident light; and
detect, based on an amount of the incident light, the occurrence of the event in a corresponding pixel of the plurality of pixels; and
the second solid-state imaging device is configured to:
capture a face of the driver; and
obtain the image data based on the captured face.

* * * * *